US006245358B1

(12) United States Patent
Adami et al.

(10) Patent No.: US 6,245,358 B1
(45) Date of Patent: Jun. 12, 2001

(54) PHARMACEUTICAL COMPOSITIONS CONTAINING POLYMER DERIVATIVE-BOUND ANTHRACYCLINE GLYCOSIDES AND A METHOD FOR THEIR PREPARATION

(75) Inventors: Marco Adami; Roberto Magrini; Paolo Maranghi; Antonino Suarato, all of Milan (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 07/997,582

(22) Filed: Dec. 28, 1992

(30) Foreign Application Priority Data

Jan. 7, 1992 (GB) .................................................. 9200247

(51) Int. Cl.[7] ............................... A61K 9/08; A61K 9/10; A61P 35/00

(52) U.S. Cl. ........................................... 424/486; 424/423

(58) Field of Search ..................................... 424/486, 423, 424/78.18, 409; 525/54.1; 514/975

(56) References Cited

U.S. PATENT DOCUMENTS

| | | | | |
|---|---|---|---|---|
| 4,062,831 | * | 12/1977 | Kopecek et al. | 526/208 |
| 4,460,560 | * | 7/1984 | Tokes et al. | 424/78.17 |
| 4,616,047 | * | 10/1986 | Lafon | 523/105 |
| 4,753,984 | * | 6/1988 | Delmotte et al. | 525/54.1 |
| 4,946,831 | * | 8/1990 | Gatti et al. | 514/34 |
| 4,968,742 | * | 11/1990 | Lewis et al. | 525/54.1 |
| 5,079,018 | * | 1/1992 | Glanow | 514/777 |
| 5,094,848 | * | 3/1992 | Brixner et al. | 424/85.91 |
| 5,135,736 | * | 8/1992 | Anderson et al. | 424/85.91 |

OTHER PUBLICATIONS

Rihova et al., "Biocompatibility of N–(2–Hydroxypropyl) Methacrylamide Copolymers Containing Adriamycin", Biomaterials, vol. 10, Jul. 1989, pp. 335–342.

Cassidy et al., "Activity of N–(2–Hydroxpropl)Methacrylamide Copolymers Containing Daunomycin Against a Rat Tumor Model", Biochemical Pharmacology, vol. 38, No. 6, (1989), pp. 875–879.

Duncan et al., "Anticancer Agents Coupled to N–(2–Hydroxypropyl)Methacrylamide Copolymers. II. Evaluation of Daunomycin Conjugates In Vivo Against L1210 Leukaemia", British J. Cancer (1988), vol. 57, pp. 147–156.

Seymour et al., "The Scientific Journal of Cancer Research Campaign", British Journal of Cancer, Sep. 1989, vol. 60, No. 3.

Busch et al., "Studies On the Metabolism of Radioactive Albumin in Tumor–Bearing Rats", Cancer Research, vol. 21, Apr. 1961, pp. 372–377.

Trouet et al., "Chemotherapy Through Lysosomes With a DNA–Daunorubicin Complex", Nature New Biology, vol. 239, Sep. 27, 1972, pp. 110–112.

Duncan et al., Anticancer Agents Coupled to N–(2–Hydroxpropyl)Methacrylamide Copolymers. 3. Evaluation of Adriamycin Conjugates Against Mouse Leukaemia L1210 In Vivo, Journal of Controlled Release, vol. 10, (1989), pp. 51–63.

Martindale, The Extra Pharmacopoeia, 1989, pp. 1264–1265, 1267, and 1275–1276, Edited by: James E.F. Reynolds, et al., Twenty–Ninth Edition.

Patent Abstracts of Japan, vol. 12, No. 47 (C–475), Feb. 12, 1988, JP-A-62 192 327, Aug. 22, 1987.

Biochemical Pharmacology, vol. 39, No. 6, pp. 1125–1132, 1990, L.W. Seymour, et al., "The Pharmacokinetics of Polymer–Bound Adriamycin".

Martindale, The Extra Pharmacopoeia, Twenty–Eighth Edition, Edited by: James E.F. Reynolds, et al., "Cetomacrogol and Nonionic Surfactants", 1982, pp. 370–379.

Patent Abstracts of Japan, vol. 14, No. 306 (C–0735), Jul. 3, 1990, JP-A-02 102 290, Apr. 13, 1990.

* cited by examiner

*Primary Examiner*—Edward J. Webman
(74) *Attorney, Agent, or Firm*—Oblon, Spivak, McClelland, Maier & Neustadt, P.C.

(57) ABSTRACT

A lyophilized composition comprising (a) a conjugate comprising a N-alkyl methacrylamide-based copolymer and an anthracycline glycoside linked through a peptide spacer to the copolymer and (b) a cosolubilizing agent may optionally also contain (c) a filler. Also optionally, a targeting moiety may be linked to the copolymer of the conjugate via a peptide spacer. An injectable solution of the conjugate is obtained by reconstitution of the lyophilized composition.

22 Claims, No Drawings

PHARMACEUTICAL COMPOSITIONS CONTAINING POLYMER DERIVATIVE-BOUND ANTHRACYCLINE GLYCOSIDES AND A METHOD FOR THEIR PREPARATION

The present invention relates to stable lyophilized formulations containing polymer-bound anthracycline glycosides.

Anthracycline antibiotics are among the most effective and widely used antitumour agents. The best known members of this class of compounds are Doxorubicin, Daunorubicin, Epirubicin and Idarubicin, which are used clinically to treat a variety of tumours. Several new derivatives have been synthesized for the purpose of finding an analogue with enhanced activity and/or lower toxicity, and some have already entered clinical trials.

Anthracycline antibiotics display good activity against human neoplasms, including some solid tumours. Toxic side-effects, including cardiomyopathy, the occurrence of which is related to the total dose of the drug, are associated to the administration of these with little preferential accumulation of the active drug in tumour tissue.

Numerous attempts have been made to improve therapeutic index and specificity of anthracyclines either by modifying their mode of delivery or by using a variety of drug delivery systems, such as liposomes, microspheres, antibodies, etc.

Synthetic polymers based on N-alkyl-methacrylamide, wherein the alkyl group may contain one or more hydroxy groups, have been proposed as potential drug carriers: see U.S. Pat. No. 4,062,831, U.S. Pat. No. 4,097,470 and EP-A-187547. Such polymers are soluble in aqueous media and have good biocompatibility.

The copolymerization of N-alkyl-methacrylamide, wherein the alkyl group contains one or more hydroxy groups, with p-nitrophenylesters of N-methacrylolyl oligopeptides gives a polymer containing oligopeptide side chains terminating in reactive p-nitrophenyl ester groups, which allow binding to many drugs containing a primary amino group, such as anthracycline glycosides and, optionally, targeting moieties containing a primary amino group.

The so formed polymer-anthracycline glycoside conjugates consist therefore of an inert polymeric carrier, which is a N-alkylmethacrylamide based copolymer, combined through peptide spacers with an anthracycline glycoside and, optionally, a targeting moiety. Preferably the inert polymeric carrier is N-(2-hydroxypropyl)methacrylamide (HMPA).

The oligopeptide spacers are cleaved only after internalization into cells by lysosomal thiol dependent proteinases (see, for example, Duncan R. et al. in Makromol. Chem. 184, 1997–2005, 1983). The targeting moieties optionally present within the polymer structure are able to interact with specific receptors on cell surfaces. For example, galactose interacts with receptors localized on plasma membrane of liver/cells. In this manner the drug is specifically delivered to cancer tissue, such as hepatoma.

The said polymer-anthracycline glycoside conjugates have been shown to possess antitumour activity in vivo, and decreased toxicity: for example, approximately 10-fold more doxorubicin can be administered in conjugate form without overt signs of toxicity (see, for example, Duncan R. et al. in Br. J. Cancer 57, 147–156, 1987; Duncan R. et al. in J. Controlled Release 10, 51–64, 1989; Cassidy J. et al. in Biochem. Pharmacol. 38, 875–880, 1989).

The synthesis of the above mentioned conjugates has also been described (see, for example, Rihova B. et al. in Biomaterials 10, 335–342, 1989).

Particular conjugates between the HPMA copolymer and the anthracycline glycosides are:

(i) a conjugate composed of x mol % of units of formula (A), y mol % of units of formula (B) and z mol % of units of formula (C):

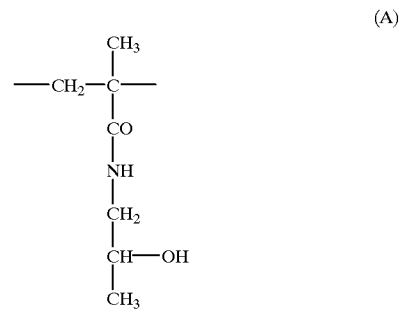

(A)

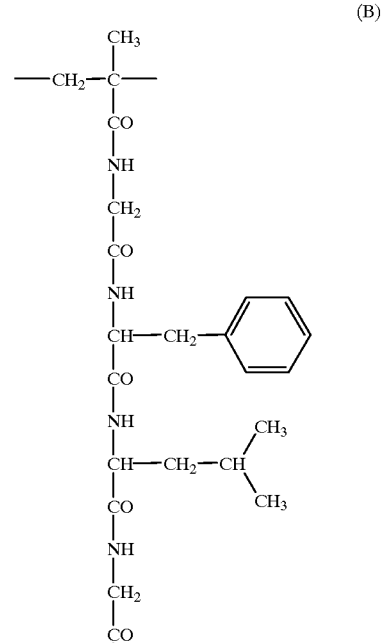

(B)

-continued

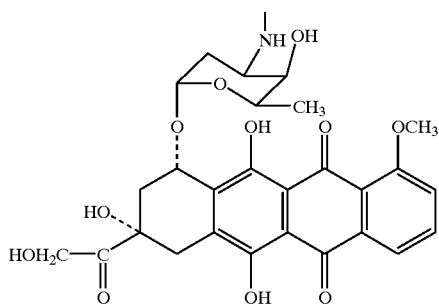

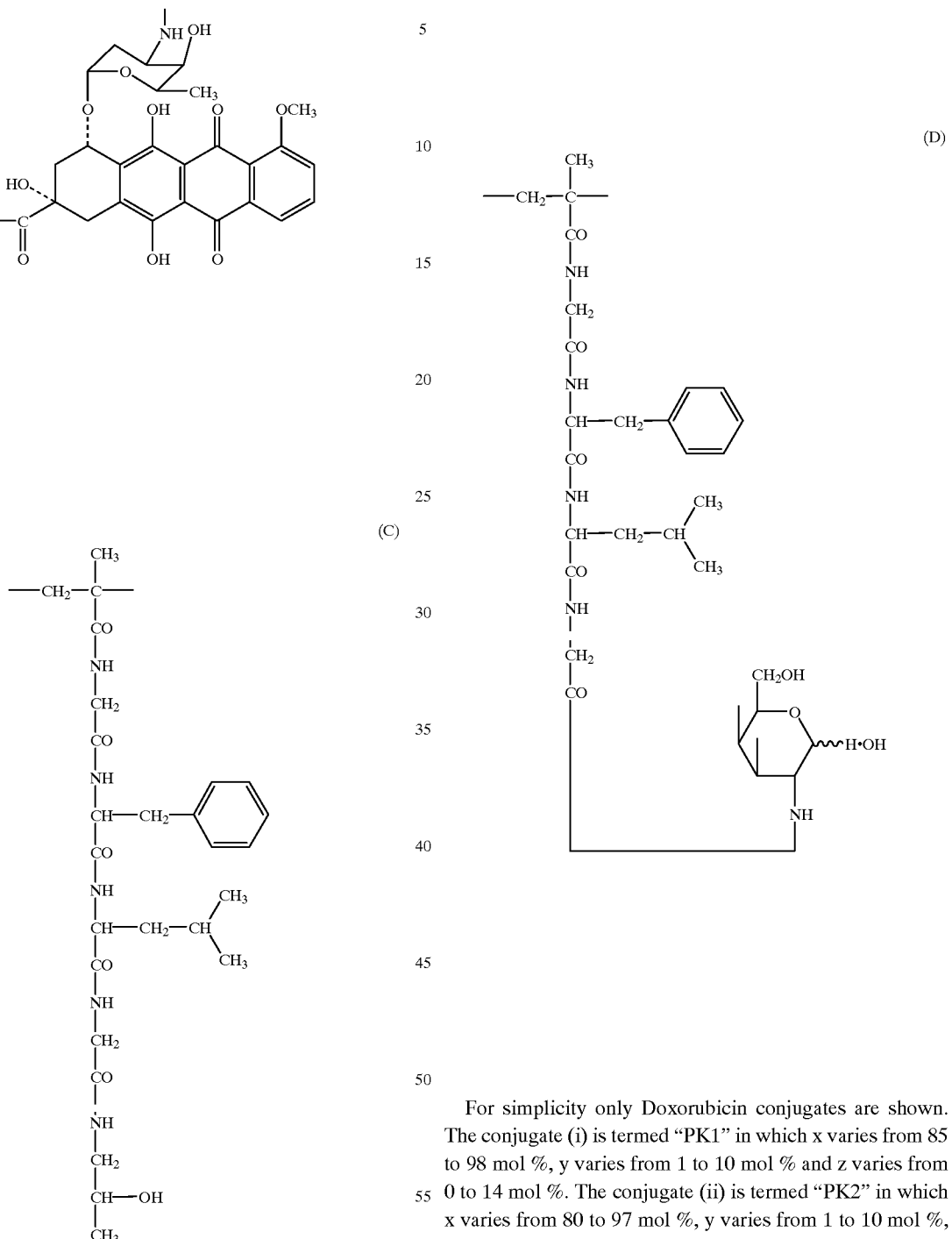

and (ii) a conjugate composed of x mol % of units of formula (A) above, y mol % of units of formula (B) above, z mol % of units of formula (D) and w mol % of units of formula (C) above:

For simplicity only Doxorubicin conjugates are shown. The conjugate (i) is termed "PK1" in which x varies from 85 to 98 mol %, y varies from 1 to 10 mol % and z varies from 0 to 14 mol %. The conjugate (ii) is termed "PK2" in which x varies from 80 to 97 mol %, y varies from 1 to 10 mol %, z varies from 0 to 18 mol % and w varies from 1 to 18 mol %. In each conjugate, the anthracycline antibiotic is linked to the HPMA copolymer by a tetrapeptide sequence attached to the sugar amine of the anthracycline by a peptide bond. This linkage is resistant to acid hydrolysis, but the glycosidic bond between the sugar amine ring and the aglycone moiety is hydrolysed relatively easily, releasing the free aglycone.

The conjugates (i) and (ii) may be shown below as formulae (I) and (II):

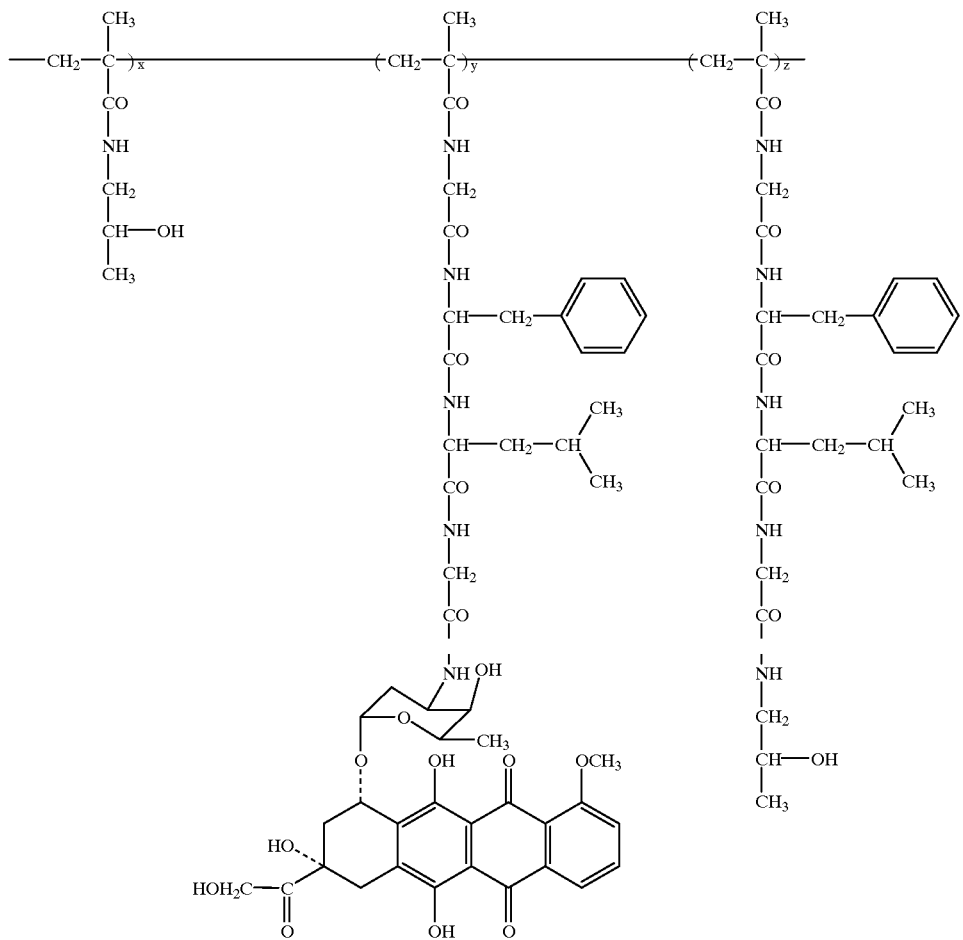
(I)
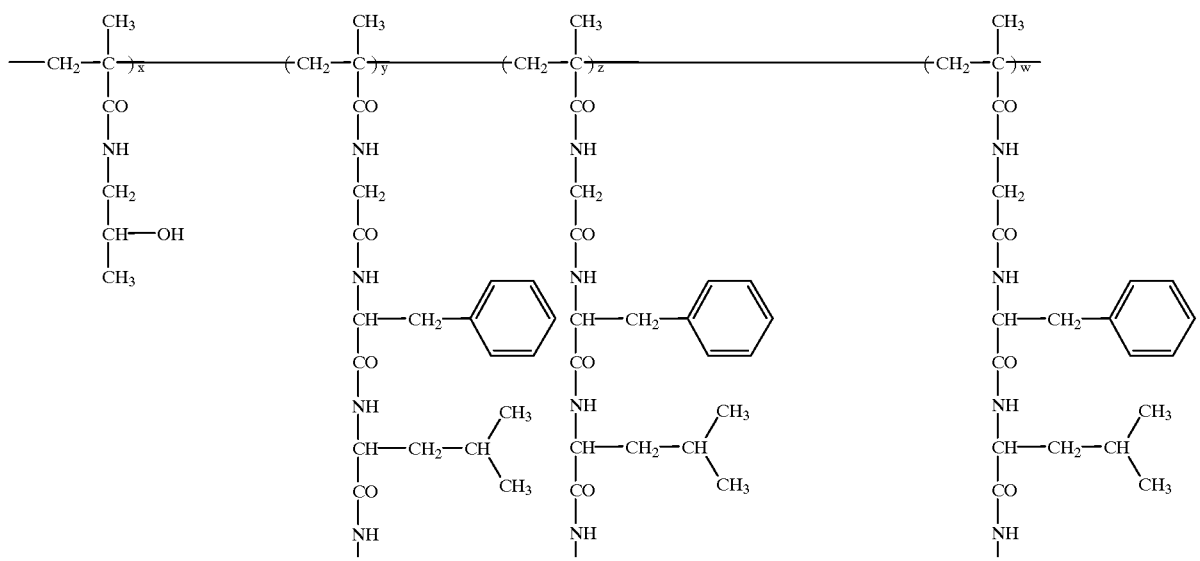
(II)

-continued

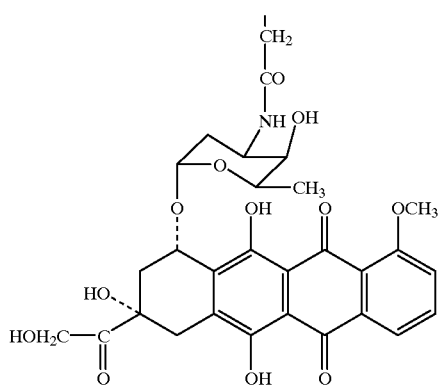 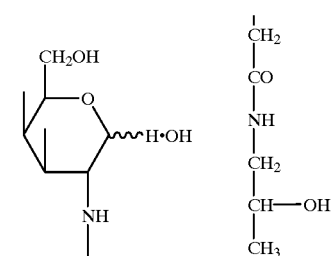

As illustrated by Seymour L. W. et al in Biochemical Pharmacology 39, 1125–1131, 1990, following intravenous administration to mice, the pharmacokinetics of Doxorubicin were markedly altered by its conjugation to HPMA copolymer: the high initial levels of free Doxorubicin in plasma observed following administration of free drug were absent in the case of polymer Doxorubicin conjugates and the subsequently high levels of free Doxorubicin seen in other tissues were also abolished. In contrast, the circulating half-life of polymer Doxorubicin conjugates was approximately 15 times longer than that of the free drug. The initial peak level of free Doxorubicin in the heart was reduced 100-fold following administration of drug-conjugate.

As high levels of anthracyclines in cardiac tissue are known to correlate with tissue damage and cumulative, delayed-onset cardiotoxicity, the decreased cardiac levels observed following administration of HPMA copolymer—Doxorubicin conjugate are a very important issue and may account for the decreased toxicity and improved efficacy reported in the literature for the polymer-conjugated drug: for example, a recent study using rats has shown a marked reduction in the toxicity of the HPMA copolymer Doxorubicin conjugate, with no evidence for any decrease in cardiac output up to 20 weeks following administration of the drug. In this study Doxorubicin was applied at 4 mg/Kg, a dose that is usually lethal when administered to rats in unconjugated form (for details, lease refer to Yeung T. K. et al in "Proceedings of the British Association for Cancer Research Meeting", Glasgow, UK, Apr. 10, 1989).

The significant reduction in the cardiac doxorubicin content using stable, covalent polymer—conjugated drug is thought to be related to the fact that these conjugates are stable in the bloodstream and are only cleaved intracellularly.

Similar HPMA copolymer—Daunomycin conjugates used to treat Walker Sarcoma in Wistar rats have been able to show both improvement in the therapeutic response compared with free Daunomycin and also a large increase in the amount of free Daunomycin detected in the tumour following administration of the polymer conjugated drug (see Cassidy J. et al in Biochem. Pharmacol. 38, 875–880, 1989). It has been speculated that this passive tumour targeting of the HPMA copolymer—Daunomycin conjugate may be related to the prolonged circulation of the drug in the bloodstream: in fact, certain tumours, including Walker Sarcoma, are known to have high rates of pinocytosis in vivo, and it has been suggested that extending the circulation times of antineoplastic drugs may elevate their relative concentrations in tumour cells (see, for example, Trouet A. et al in Nature New Biol. 239, 110–112, 1972, and Busch H. et al in Cancer Res. 21, 371–377, 1981).

We have now investigated the formulation of anthracycline-HPMA copolymer conjugates. We found that, although the aqueous equilibrium solubility of polymer-anthracycline glycoside conjugates is sufficiently high (>5% w/v), these polymers have got a remarkable hydrophobicity so that their dissolution rates in water were quite slow. Hence we found that, if lyophilized alone, anthracycline-HPMA copolymer conjugates formed a freeze-dried cake which dissolved very slowly. Complete dissolution took a very long time, i.e. even more than 30 minutes with continuous shaking. This is disadvantageous because of the recognized toxicity of the anthracycline glycosides family.

Moreover we found that, after reconstitution with sterile water or with sterile physiological saline or with any other aqueous physiological diluent, some undissolved fragments of the polymer were entrained on the top of the froth and/or got caught on both the rubber stopper and the vial walls. This problem is of particular relevance because of the risk of administering intravenously some undissolved particles. However, we did find that the presence of a particular cosolubilizing agent in a freeze-dried preparation containing a polymer-anthracycline glycoside conjugate enhanced the solubility of the drug to a great extent, so that upon reconstitution complete dissolution of the conjugate may be achieved in less than one minute without any difficulty.

Accordingly, the present invention provides a lyophilized composition comprising (a) a conjugate comprising a N-alkyl methacrylamide-based copolymer and an anthracycline glycoside linked through a peptide spacer to the copolymer and (b) a cosolubilizing agent. Optionally a targeting moiety is linked through a peptide spacer to the polymer. Also optionally, the composition further comprises (c) a filler.

It is therefore possible to provide a lyophilized pharmaceutical composition containing a polymer-anthracycline glycoside conjugate and having reduced dissolution time when reconstituted with an aqueous pharmaceutically acceptable diluent, so as to permit the practical and safe use of polymer-anthracycline conjugates in therapy. In the present specification the terms "pharmaceutical", "pharmaceutically" and the like are meant to refer to applications in both human and veterinary field. The terms "llyophilized" and "freeze-dried" are used without distinction.

The copolymer to which the anthracycline glycoside is linked consists essentially of units derived from a N-alkyl methacrylamide. Preferably the alkyl group is a $C_1$–$C_6$ alkyl group. The alkyl group may contain one or more hydroxy groups. A suitable alkyl group may therefore be a $C_1$–$C_4$ alkyl group substituted by a hydroxy group. A preferred alkyl group is a 2-hydroxy-propyl group. A preferred copolymer is a copolymer of N-(hydroxypropyl) methacrylamide (HPMA).

The copolymer also consists essentially of other units derived from a methacryloyl monomer. The anthracycline glycoside is linked to these units via a peptide spacer. The units may therefore be considered as being derived from a N-methacryloylated peptide, the anthracycline being linked to the peptide. The units may be represented by formula (III):

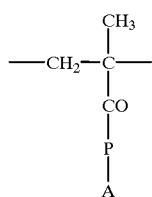

(III)

in which P denotes the peptide spacer and A denotes the anthracycline glycoside.

The copolymer may comprise too yet other units which are derived from a methacryloyl monomer and to which a targeting moiety is linked via a peptide spacer. These units may therefore be considered as being derived from a N-methacryloylated peptide, the targeting moiety being linked to the peptide. The units may be represented by formula (IV):

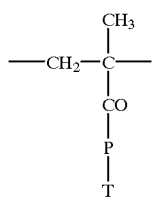

(IV)

in which P denotes the peptide spacer and T denotes the targeting moiety.

The copolymer typically contains the units derived from a N-alkyl methacrylamide in a proportion of 60 mol % or more, for example at least 80 mol % or at least 85 mol %. These units may be present in an amount up to 97 or 98 mol %. The units of formula (III) may be present in a proportion of from 1 to 20 mol %, for example from 1 to 10 mol %. The units of formula (IV) may be present in an amount of from 0 to 20 mol %, for example from 0 to 18 mol % or from 0 to 14 mol %.

A preferred copolymer is copolymer of 1-[methacryloyl] amino-2-hydroxy-propane and N-methacryloyl-peptidyl anthracycline and, optionally, 1-[methacryloyl peptidyl] amino-2-hydroxy propane and a N-methacryloyl-peptidyl targeting moiety. More specifically, the copolymer may be a copolymer of x mol % of {1-[methacryloyl]amino-2-hydroxypropane units; y mol % of {-N-[methacryloyl-(P)](A)} units;

optionally, z mol % of {1-[methacryloyl-(P)]amino-2-hydroxypropane} units; and w mol % of {-N-[methacryloyl-(P)](T)} units
wherein P is the peptide spacer A is the anthracycline glycoside T is the targeting moiety
and x, y, z and w represent the molar percentages of the components. These percentages may vary within broad ranges such as from 80 to 98% for x; from 1 to 10% for y; from 0 to 18% for z and from 1 to 18% for w.

Suitable conjugates are conjugates PK1 and PK2 mentioned above. For the PK1 conjugate, these values may vary from about 85 to 98 mol/mol % for x; about 1 to 10 mol/mol % for y; and about 0 to 14 mol/mol % for z. For the PK2 conjugate the values may vary from about 80 to 97 mol/mol % for x, about 1 to 10 mol/mol % for y, about 0 to 18 mol/mol % for z and about 1 to 18 mol/mol % for w.

The anthracycline glycoside covalently bound to the copolymers via the peptide spacers may be any anthracycline glycoside, for example one of those disclosed in GB-A-1161278, GB-A-1217133, GB-A-1457632, GB-A-1467383, GB-A-1500421 and GB-A-1511559. In particular, the anthracycline glycoside is, for example, doxorubicin, 4'-epi-doxorubicin (i.e. epirubicin), daunorubicin and 4-dimethoxy-daunorubicin (i.e. idarubicin).

The peptide spacer may be from 1 to 10, for example from 2 to 4, amino acid residues long. The spacer should be susceptible to intracellular lysosomal hydrolysis. The spacer may be resistant to extracelluar hydrolysis. Suitable spacers were disclosed in EP-A-187547. In particular, the spacer may be Gly-Leu-Gly; Gly-Phe-Ala; Gly-Leu-Phe; Gly-Leu-Ala; Gly-Phe-Leu-Gly; Gly-Phe-Phe-Leu; Gly-Leu-Leu-Gly or Gly-Phe-Phe-Gly. Preferably the peptide spacer is Gly-Phe-Leu-Gly. Typically, one type of peptide spacer only is carried by the N-alkyl methacrylamide-based copolymers so that the anthracycline glycoside and, if present, targeting moiety are linked to the copolymer through the same type of spacer.

The targeting moiety is typically a saccharide, especially a monosaccharide or a disaccharide. Preferably the targeting moiety is galactose, galactosamine, glucosamine, mannosamine, fucosylamine or lactosamine. Alternatively, the targeting moiety may be a monoclonal antibody, for example a monoclonal antibody specific for a human neoplasm such as a neoplasm of the breast, colon, lung, prostate, ovary or thymus.

The polymer anthracycline conjugates employed in the compositions of the present invention may be, for example, those disclosed in U.S. Pat. No. 4,097,470 and EP-A-187547, or similar conjugates. They may be prepared by known procedures, for example by procedures similar to those reported in these documents.

The cosolubilizing agent used as a solubility enhancer in the lyophilized preparation of the invention is typically a surfactant selected for example from polyethylene sorbitan fatty acid esters (known generally as polysorbates), polyethylene-polypropylene glycol polymers (known generally as poloxamers), polyethylene glycol esters of fatty acids, and phosphatides. The surfactant should be non-toxic and acceptable for intravenous administration.

Useful polyoxyethylene sorbitan fatty acid esters include partial $C_{12-20}$ saturated or unsaturated fatty acid esters of sorbitol and its mono- and di-anhydrides copolymerised with ethylene oxide. Typically, from 10 to 40, for example about 20 moles of ethylene oxide for each mole of sorbitol and its anhydrides will be present.

Preferably the polysorbate is polysorbate 20 (polyoxyethylene 20 sorbitan monolaurate, Chemical Abstract ref. No. 9005-64-5, which is a mixture of partial lauric acid esters of sorbitol and its mono- and di-anhydrides copolymerized with approximately 20 moles of ethylene oxide for each mole of sorbitol and its anhydrides) or polysorbate 80 (polyoxyethylene 20 sorbitan monooleate, Chemical Abstract ref. No. 9005-65-6). Other suitable polysorbates are polysorbate 40 (polyoxyethylene 20 sorbitan monopalmitate, CAS No 9005-66-7), polysorbate 60 (polyoxyethylene 20 sorbitan mono-stearate CAS No 9005-67-8), polysorbate 65 (polyoxyethylene 20 sorbitan tristearate, CAS No. 9005-71-4) and polysorbate 85 (polyoxyethylene 20 sorbitan trioleate CAS No 9005-70-3).

Poloxamers include non-ionic surfactants with the structure $HO(CH_2—CH_2—O)_a—(CH(CH_3)CH_2O)_b—(CH_2—CH_2—O)_aH$ where b is an integer from 15 to 67 and a is an integer from 2 to 98. Preferably the Poloxamer is Poloxamer 188. Poloxamer 188 is one of a series of poly(oxyethylene)-poly(oxypropylene) block copolymers which may be used as a cosolubilising agent. In the formula above, a is 75 and b is 30 for Poloxamer 188 which thus has a molecular weight of 8350.

The polyethylene glycol esters of fatty acids are, preferably, polyoxyethylene stearates. The phosphatide is preferably a lecithin, for example egg or soya lecithin.

All the surfactants require co-lyophilization with the drug to exert their activity as dissolution enhancers. If they acted simply by decreasing the surface tension of the drug-containing solution or by a wetting effect, they should be equally active if either co-lyophilized with the drug or added to the reconstitution solvent. Co-lyophilization being required, this accounts for some unexpected interaction with the drug, which takes place in the solid state.

The relative proportions of the conjugate and cosolubilizing agent in the preparations of the invention are generally such that, per 10 parts by weight of conjugate, there are from about 0.01 to 1.0, preferably from 0.035 to 0.35, parts by weight of cosolubilizing agent. A particularly preferred weight ratio between the cosolubilizer and the conjugate is 0.1–0.2:10.0. This optimum ratio combines the good performance of the cosolubilizer as dissolution enhancer with its pharmaceutical acceptability, from a toxicological point of view. The use of more elevated amounts of surfactant is severely limited for toxicity and tolerability reasons.

The lyophilized formulations may contain the polymer-anthracycline glycoside conjugate in varying amounts. Typical formulations contain, for example, a quantity of polymer anthracycline glycoside conjugate equivalent to 5, 10, 20, 25 or 50 mg of anthracycline glycoside.

In addition to the cosolubilizer, the composition of the present invention may further contain auxiliary ingredients, whose presence may help to provide a rapidly soluble freeze-dried product. These include fillers (or diluents, or extenders) and an organic solvent.

Fillers are generally used in lyophilization technology for facilitating the process and/or providing mechanical integrity to the lyophilized cake. However, fillers need not be present in the case of the present invention, as the polymer-anthracycline conjugates can be easily lyophilized with no additives, to form a firm and rigid cake. As used herein, the word "filler" means a freely water soluble, solid particulate diluent which, when co-lyophilized with the polymer-anthracycline glycoside conjugate, may help solubilization of a slowly dissolving polymer upon addition of the reconstitution solvent by providing a "dragging" effect due to its high hydrophilicity.

The water soluble filler suitable for use in the present invention can be any of the pharmaceutically acceptable inert solid materials typically used for lyophilization. Such fillers include, for example, sugars such as glucose, maltose, sucrose, and lactose; polyalcohols such as sorbitol and mannitol; amino acids such as glycine; polymers such as polyvinylpyrrolidone; polysaccharides such as dextran; certain inorganic salts such as sodium or potassium phosphates, or sodium chloride. In a preferred embodiment, the filler is lactose.

The ratio of the weight of the polymer-anthracycline glycoside conjugate to the weight of the filler used in the compositions of the present invention should generally be within the range of from about 0.1:1 to about 20:1. In a preferred embodiment, the polymer-anthracycline glycoside conjugate:filler ratio is from about 1.0:1 to about 2.5:1. The amount of the filler is linked to that of the conjugate and is critical to the dissolution behaviour of the lyophilized cakes.

If the filler is used alone (i.e. without any cosolubilizer), complete reconstitution takes a somewhat long time, e.g. from not less than 8–10 minutes up to more than 20–30 minutes depending on the relative amounts of both the filler and the conjugate polymer. This point is illustrated in details in Experiment 1.

If the filler and the cosolubilizer are both present in the formulation, the reconstitution time is markedly reduced, ranging from about 30–90 seconds to about 4–5 minutes, depending on the quantities of the conjugate, the filler and the cosolubilizer. Generally, the higher the ratio between the cosolubilizer and the conjugate, the less the reconstitution time.

Quite surprisingly, therefore, we have found that the filler and the cosolubilizer may act synergistically as dissolution enhancers. Moreover, we have unexpectedly found that the presence of a filler also helps dissolution of the conjugate during the manufacturing of the solution to be freeze-dried. Therefore, the presence of a filler in the formulations of the present invention even if not strictly mandatory, is highly preferred. Experiments 1 and 2 illustrate this point in details.

The invention also provides a method for producing a stable rapidly soluble lyophilized composition according to the invention, which method comprises a) mixing, in an aqueous solution, the polymer-anthracycline conjugate, the cosolubilizing agent and, optionally, the filler and/or an organic solvent;

b) freeze-drying the aqueous solution.

Organic solvents are not commonly used in lyophilization technology. They are not as easy to handle as water and their use is also limited by the fact that parenteral freeze-dried dosage forms cannot be allowed to contain elevated residues of organic solvents for toxicity reasons. However, it is generally recognized that organic solvents may have certain useful properties, such as:

promotion of the solubilization of a drug during the manufacturing of the solution to be freeze-dried (this is not important in the case of the present invention as the polymer anthracycline glycoside conjugates are more soluble in water than in alcohol, isopropanol, and the like);

reduction of the degradation rate of the active material in water during processing; and induction of crystallization of a drug in the frozen state.

Unexpectedly, though, we found that the presence of an organic solvent in the solution to be freeze-dried further enhances the dissolution rate of the lyophilized product. A small concentration of organic solvent is effective, typically less than 5% v/v and preferably less than 1% v/v, with reference to the solution to be freeze-dried. 0.5% v/v or more of an organic solvent may therefore be employed. Experiment 2 illustrates this point.

Organic solvents suitable for use in the present invention include ethanol, isopropanol, tert-butanol, and any other pharmaceutically acceptable solvent which is easily removed during the freeze-drying process, so that the finished lyophilized product contains only residues (if any) of such solvent, thus allowing parenteral administration with no toxicity and/or tolerability risks. The solvent is typically a water-miscible organic solvent. Preferred organic solvents for this purpose are organic aliphatic alcohols, in particular $C_1$–$C_4$ alkanols such as ethanol.

The present invention also provides a kit containing a lyophilized composition according to the invention in a sterile vial and a sterile solution for reconstituting the said lyophilized composition.

The present invention further includes a method for preparing an injectable solution of polymer anthracycline glycoside conjugate, characterized by dissolving, in a solution suitable for injection, a stable, rapidly soluble, lyophilized preparation comprising a polymer-anthracycline conjugate, a cosolubilizer, and optionally a filler.

The lyophilized formulations disclosed by the present invention may be prepared in a conventional way, following the usual freeze-drying techniques while taking, however, all precautions required in manipulation of toxic substances such as anthracycline glycosides. Thus, for example, the cosolubilizer, the filer and the polymer anthracycline glycoside conjugate are successively dissolved under stirring in a suitable amount of deaerated water for injections, possibly containing the organic solvent. Then, further water is added to reach the desired final volume. The resulting solution is clarified and sterile filtered and aseptically distributed in sterile containers (vials) of desired capacity. Freezing of the solution, e.g. at −40° C. to −50° C. for about 4 to 5 hours, and drying, e.g. at a final temperature of 30°–40° C. for about 6 to 8 hours is then performed and the vials are sealed according to usual procedures.

Also, the reconstitution of the freeze-dried preparations, e.g., with sterile water, physiological saline solution, or any pharmaceutically acceptable isotonic solution, is performed in conventional manner. Thus, for example, the physiological saline solution (0.9% sodium chloride aqueous solution) is used in a volume which may vary depending on the type and the amount of the active polymer contained in the lyophilized cake: volumes from 5 mL to 25 mL of physiological saline solution may be, e.g., used for reconstituting amounts of polymer equivalent to 5 mg and 50 mg, respectively, of anthracycline glycoside. The injectable reconstituted solutions of the invention are administered either by rapid intravenous injection or (preferably) by intravenous infusion, according to a variety of possible dose schedules.

The reconstituted compositions of the invention are useful for treating tumours in both human and animal hosts. They can be employed to improve the condition of a patient having a tumour. Examples of tumours that can be treated are, for instance, sarcomas, including osteogenic and soft tissue sarcomas, carcinoma, e.g., breast-, lung-, bladder-, thyroid-, prostate- and ovarian carcinoma, lymphomas, including Hodgkin and non-Hodgkin lymphomas, neuroblastoma, melanoma, myeloma, Wilms tumour, and leukemias, including acute lymphoblastic leukaemia and acute myeloblastic leukaemia.

The following Experiments and Examples illustrate but do not limit the invention in any way. They clearly show that the formulations of the present invention assure a considerable saving of time, a reduction in the hazards of operator exposure, and a safe administration to patients.

Experiment 1

Influence of the cosolubilizer and of the filler on the dissolution time of freeze-dried preparations containing polymer Doxorubicin conjugate (PK1 conjugate) was examined. The following formulations were freeze-dried:

| Trial No | PK1 mg | Lactose mg | Polysorbate 80 mg | W.F.I. (a) |
|---|---|---|---|---|
| 1 | 70 (b) | — | — | q.s. to 1.0 mL |
| 2 | 70 (b) | 50 | — | q.s. to 1.0 mL |
| 3 | 70 (b) | 140 | — | q.s. to 2.0 mL |
| 4 | 70 (b) | 140 | 2 | q.s. to 2.0 mL |

(a) W.F.I. = Water for Injections
(b) Equivalent to approximately 5 mg of Doxorubicin Reconstitution of the lyophilized preparations was performed either with sterile water or with Sodium Chloride Injection.

Times for complete reconstitution were as follows:

| Trial No. | Time (min.) | |
|---|---|---|
| 1 | about 60 | (with both solvents) |
| 2 | about 40 | (with both solvents) |
| 3 | 15–20 | (with both solvents) |
| 4 | less than 1 | (with both solvents) |

Experiment 2

Influence of the simultaneous presence of the cosolubilizer and of the filler (with and without organic solvent in the freeze drying process) was examined for polymer-Doxorubicin conjugate (PK2 conjugate).

The following formulations were freeze-dried:

| Trial No | PK1 mg | Lactose mg | Polysorbate 80 mg | Ethanol mL | W.F.I. |
|---|---|---|---|---|---|
| 1 | 700(a) | — | 10 | — | qs to 15 mL |
| 2 | 700(a) | 450 | 10 | — | qs to 15 mL |
| 3 | 700(a) | 300 | 3 | — | qs to 15 mL |
| 4 | 700(a) | 450 | 10 | 0.1 | qs to 15 mL |
| 5 | 700(a) | 300 | 10 | 0.1 | qs to 20 mL |
| 6 | 700(a) | 450 | 5 | 0.1 | qs to 15 mL |

(a)Equivalent to approximately 50 mg of Doxorubicin.

The following results were obtained (reconstitution with sterile water):

| Trial No. | Time for complete dissolution (min.) |
|---|---|
| 1 | 4–5 |
| 2 | 1.5 |
| 3 | 4–5 |
| 4 | 0.75–1.5 |
| 5 | 1.0–1.5 |
| 6 | 1.0–1.5 |

EXAMPLE 1

Polymer-bound Doxorubicin formulations were prepared by following the procedure reported below. The relative proportions of the various components employed in the preparation were as hereinbelow indicated (amounts are per vial):

| | | |
|---|---|---|
| PK2 | 700 mg (equivalent to approx. 50 mg of Doxorubicin) | |
| Lactose | 600 mg | |
| Polysorbate 80 | 10 mg | |
| Hydrochloric acid | qs to pH = 5.0 | |
| Ethanol | 0.1 mL | |
| Water for injections | qs to 15.0 mL | |

Lactose, polysorbate 80 and PK2 were subsequently dissolved under stirring into W.F.I., deaerated by nitrogen bubbling (about 90% of the finally required water volume). After adjusting pH to 5.0 with hydrochloric acid, ethanol was added.

The solution was then brought to the final volume with deaerated W.F.I. The solution was then filtered under sterile conditions through a 0.22 μm microporous membrane. Volumes of 15.0 mL of solution were aseptically distributed into sterile, type I colourless glass vials having 50–56 mL capacity.

The solutions were frozen in the vials at a temperature of −40 to −45° C. for 4 to 5 hours. Lyophilization was then carried out, drying the product, in the final stage, at about 40° C. for 5 to 6 hours.

Vials were closed with sterile chlorobutyl rubber stoppers and sealed with aluminium caps.

Complete dissolution of the freeze-dried cakes (reconstitution either with sterile water or Sodium Chloride Injection ) took approximately 60 seconds.

Following an analogous procedure, an identical $Pk_1$ polymer-bound Doxorubicin formulation was prepared.

EXAMPLE 2

Operating in analogous fashion as described in Example 1, the following lyophilized formulations were prepared (amounts are per vial):

| | | Trial No | | |
|---|---|---|---|---|
| | | 1 | 2 | 3 |
| PK2 | mg | 700 | 700 | 700 |
| Lactose | mg | 450 | 450 | 450 |
| Polysorbate 80 | mg | 10 | 10 | 10 |
| Ethanol | mL | — | 0.1 | — |
| Isopropanol | mL | — | — | 0.2 |
| Hydrochloric acid q.s. to | pH | 5.0 | 5.0 | 5.0 |
| W.F.I. q.s. to | mL | 15.0 | 15.0 | 15.0 |

Complete dissolution of the freeze-dried cakes (reconstitution either with sterile water or Sodium chloride Injection) took approximately 0.75–1.5 minutes.

EXAMPLE 3

Operating in analogous fashion as described in Example 1, the following lyophilized formulations were prepared (amounts are per vial):

| | | Trial No | | | |
|---|---|---|---|---|---|
| | | 1 | 2 | 3 | 4 |
| PK2 | mg | 700 | 700 | 700 | 700 |
| Lactose | mg | 300 | — | 300 | — |
| Mannitol | mg | — | 300 | — | 300 |
| Polyoxyethylene stearate | mg | 5.0 | 5.0 | — | — |
| Poloxamer 188 | mg | — | — | 5.0 | 5.0 |
| Hydrochloric acid qs to | pH | 5.0 | 5.0 | 5.0 | 5.0 |
| W.F.I. qs to | mL | 20.0 | 20.0 | 20.0 | 20.0 |

Complete dissolution of the freeze-dried cakes (reconstitution with 25 mL of sterile water) was achieved within 3 to 5 minutes.

EXAMPLE 4

Operating in analogous fashion as described in Example 1, the following lyophilized formulations were prepared (amounts are per vials—type I colourless glass vials having 8–10 mL capacity were used):

| | Trial No | | |
|---|---|---|---|
| | 1 | 2 | 3 |
| PK1 | 70 | — | — |
| PK2 | — | 70 | 70 |
| Lactose | 70 | 30 | — |
| Polysorbate 80 | 0.2 | 0.2 | 0.2 |
| Sodium Chloride | 20 | 20 | 20 |
| W. F. I. | 2.0 | 2.0 | 2.0 |

Complete dissolution of the freeze-dried cakes (reconstitution with 2.5 mL of either sterile water or Sodium Chloride Injection) was obtained within 0.5 minutes.

EXAMPLE 5

Stability of Compositions of the Invention

Freeze-dried vials containing compositions according to the present invention comprising about 50 mg of bound Doxorubicin were examined for long term stability over various periods of time at different temperatures.

The following parameters were examined and the acceptable standards are also given.

Appearance: colourless glass vials, containing a porous red, freeze-dried cake or mass, determined by visual inspection total doxorubicin content: U.V. spectrophotometric method
related substances: HPLC method
water: not more than 3%
time for reconstitution*: not more than 3 minutes
appearance after reconstitution*: clear and clean red solution, essentially free from visible particles of foreign matter
pH after reconstitution*: 4.5–7.0

* The contents of the vials are dissolved in 25 mL of Water for Injections, BP.

The U.V. spectrophotometric method employed is as follows:

Materials

Doxorubicin HCl, working standard

Methanol, UV grade
Water for Injections, B.P. grade
2N hydrochloric acid, ACS grade
50 mg (Doxorubicin equivalent) PK1 freeze-dried vials
50 mg (Doxorubicin equivalent) PK2 freeze-dried vials
High precision laboratory glassware
Equipment
UV-Visible Spectrophotometer, PHILIPS mod. PU 8740, or equivalent.
Printer plotter, PHILIPS mod. 357820, or equivalent.
Solutions
Solvent for the spectrophotometric measurements:
   Transfer 5 ml of 2N HCl into a 1000 ml volumetric flask and fill to the mark with methanol (Solvent S).
Standard solution
   Transfer about 10.7 mg, exactly weighed, of Doxorubicin HCl working standard, corresponding to about 10 mg of Doxorubicin as free base, into a 50 ml volumetric flask and dissolve to volume with the Solvent S (Solution A).
   Dilute 10.0 ml, exactly measured, of the Solution A to 50 ml with the Solvent S, in volumetric flask.
Sample solution
   Dissolve the contents of the freeze-dried vials of 50 mg (Doxorubicin equivalent) PK1 or PK2 in 25 ml of Water for Injections.
   Transfer 2.0 ml, exactly measured, into a 100 ml volumetric flask and dilute to volume with Solvent S.
Analytical Procedure
   Register in 1 cm pathlength cells the spectra of the standard and sample solutions in the 350–550 nm range and read the adsorbance at the maximum wavelength (478 nm), using the Solvents as a blank.
The HPLC methodology is as follows:
Materials
Doxorubicin HCl, working standard
PK1 drug substance, working standard
PK2 drug substance, working standard
Acetonitrile, HPLC grade
Water, HPLC grade
Trifluoroacetic acid, HPLC grade
2N sodium hydroxide, analytical grade
85% phosphoric acid, analytical grade
50 mg (Doxorubicin equivalent) PK1 freeze-dried vials
50 mg (Doxorubicin equivalent) PK2 freeze-dried vials
Equipment
Liquid chromatography Milton Roy CM 4000, or equivalent, equipped with:
   chromatographic column: Vydac C18 (length: 250 mm, internal diameter: 4.6 mm), supplied by the Separations Group, Hesperia, Calif. (USA)
   injection valve: Rheodyne model 7125, or equivalent, fitted with a 50 $\mu$l sample loop
   detector: Milton Roy model 3100 or equivalent
Membrane filter, 0.22 $\mu$m porosity, Millipore Durapore GVWP, or equivalent
High precision laboratory glassware
Solutions Preparation
Mobile phase A consisting of water, containing 0.1% of trifluoroactic acid (v/v), filtered through the membrane filter and deaerated.
Mobile phase B consisting of acetonitrile, containing 0.07% trifluoroacetic acid (v/v), filtered through the membrane filter and deaerated.

Doxorubicin HCl standard solution Transfer about 5 mg, exactly weighed, of Doxorubicin HCl working standard into a 100 ml volumetric flask and dissolve to volume with water, HPLC grade. Dilute 5 ml, exactly measured, of this solution into a 50 ml volumetric flask with water/acetonitrile 70/30, HPLC grade.

PK1 or PK2 standard solution Transfer an amount of the PK1 or PK2 polymer, working standard, exactly weighed and corresponding to about 10 mg of Doxorubicin HCl into a 50 ml volumetric flask and dissolve to volume with water/acetonitrile 70/30, HPLC grade.

Sample solution
   Dissolve the contents of a 50 mg (Doxorubicin equivalent) freeze-dried vial with 25 ml, exactly measured, of water, HPLC grade. Dilute 1 ml, exactly measured, into a 10 ml volumetric flask with water/acetonitrile 70/30, HPLC grade.

Resolution solution
   Transfer about 10 mg of Doxorubicin HCl into a 100 ml volumetric flask, dissolve with 5 ml of water, HPLC grade, add 5 ml of phosphoric acid, and allow to stand for about 30 minutes. Adjust with 2N sodium hydroxide (about 37 ml) to a pH of 2.6±0.1, and fill to the mark with water, HPLC grade. (NOTE: portions of this solution may be frozen until needed, then thawed, and mixed before use).

Chromatographic Conditions

The sample solution, the Doxorubicin HCl standard solution, and the PK1/PK2 standard solutions, are alternately injected into the liquid chromatograph at the following experimental conditions:

| Column temperature | : room temperature (22° C.–24° C.) | | |
|---|---|---|---|
| Mobile phase flow-rate | : 1.0 ml/min | | |
| Analytical wavelength | : 254 ± 1 nm | | |
| Gradient conditions | : time (min) | %A | %B |
| | 0 | 70 | 30 |
| | 10 | 70 | 30 |
| | 15 | 20 | 80 |
| | 20 | 0 | 100 |
| | 25 | 0 | 100 |
| | 27 | 70 | 30 |
| Injection volume | : 50 $\mu$l | | |
| Integrating recorder attenuation | :0–10 minutes, 64 >10 minutes, 512 | | |
| Chart speed | : 0.5 cm/min | | |

Under these conditions, Doxorubicin HCl has a retention time of about 5 minutes, the PK2 and the PK2 polymers conjugated with Doxorubicin have a retention time of about 16–17 minutes.

The results obtained from studies of stability, for the formulations illustrated in example 1, are reported in the following Tables 1 to 5 for the $PK_1$ formulation and in the following Tables 6 to 10 for the $PK_2$ formulation with reference to one batch of both $PK_1$ and $PK_2$ freeze-dried vials.

TABLE 1

Long-term stability data of PK1 50 mg (as Doxorubicin) freeze-dried vials
Batch No. TF/23874
Active Drug Substance Batch No. 0019

| Test | Initial control | Refrigerator Temperature* | | | | | | |
|---|---|---|---|---|---|---|---|---|
| | | 1 mo | 2 mos | 3 mos | 6 mos | 9 mos | 12 mos | 18 mos |
| Appearance | A | UNCHANGED | | | | | | |
| Assay (U.V. method) | | | | | | | | |
| mg/vial | 50.99 | 49.25 | 44.80 | 46.79 | 49.34 | | | |
| % initial | 100.0 | 96.6 | 87.9 | 91.8 | 96.8 | | | |
| Free doxorubicin content % (HPLC method) | 1.04 | 2.49 | 2.40 | 2.21 | 2.10 | | | |
| Water % | 1.3 | n.d. | n.d. | n.d. | n.d. | | | |
| Reconstituted solution** | | | | | | | | |
| Reconstitution time (min) | 1.5 | 1.5 | 1.5 | 2.0 | 1.5 | | | |
| Appearance | B | UNCHANGED | | | | | | |
| pH | 5.42 | 5.25 | 5.25 | 4.75 | 5.65 | | | |

*2°–8° C.
**25 ml of Water for Injections, BP
n.d. = not determined
A = colourless glass vials containing a porous, red freeze-dried cake or mass
B = clear and clean red solution, essentially free from visible particles of foreign matter

TABLE 2

Long-term stability data of PK1 50 mg (as Doxorubicin) freeze-dried vials
Batch No. TF/23874
Active Drug Substance Batch No. 0019

| Test | Initial control | 25° C. | | | | | |
|---|---|---|---|---|---|---|---|
| | | 2 mos. | 3 mos. | 6 mos. | 9 mos. | 12 mos. | 18 mos. |
| Appearance | A | UNCHANGED | | | | | |
| Assay (U.V. method) | | | | | | | |
| mg/vial | 50.99 | 48.50 | 47.46 | 47.63 | | | |
| % initial | 100.0 | 95.1 | 93.1 | 93.4 | | | |
| Free doxorubicin content % (HPLC method) | 1.04 | 2.32 | 2.11 | 2.10 | | | |
| Water % | 1.3 | n.d. | n.d. | n.d. | | | |
| Reconstituted solution** | | | | | | | |
| Reconstitution, time (min) | 1.5 | 1.5 | 2.0 | 1.5 | | | |
| Appearance | B | UNCHANGED | | | | | |
| pH | 5.42 | 5.04 | 4.80 | 4.95 | | | |

**25 ml of Water for Injections, BP
n.d. = not determined
A = colourless glass vials containing a porous, red freeze-dried cake or mass
B = clear and clean red solution, essentially free from visible particles of foreign matter

TABLE 3

Accelerated stability data of PK1 50 mg (as Doxorubicin) freeze-dried vials
Batch No. TF/23874
Active Drug Substance Batch No. 0019

| Test | Initial control | 35° C. | | | | |
|---|---|---|---|---|---|---|
| | | 1 mo. | 3 mos. | 6 mos. | 9 mos. | 12 mos. |
| Appearance | A | UNCHANGED | | | | |
| Assay (U.V. method) | | | | | | |
| mg/vial | 50.99 | 49.95 | 46.89 | 46.48 | | |
| % initial | 100.0 | 98.0 | 92.0 | 91.2 | | |
| Free doxorubicin content % (HPLC method) | 1.04 | 2.23 | 2.07 | 2.09 | | |
| Water % | 1.3 | n.d. | n.d. | n.d. | | |
| Reconstituted solution** | | | | | | |
| Reconstitution time (min) | 1.5 | 2.0 | 2.0 | 1.7 | | |
| Appearance | B | UNCHANGED | | | | |
| pH | 5.42 | 5.60 | 4.95 | 4.70 | | |

**25 ml of Water for Injections, BP
n.d. = not determined
A = colourless glass vials containing a porous, red freeze-dried cake or mass
B = clear and clean red solution, essentially free from visible particles of foreign matter

TABLE 4

Accelerated stability data of PK1 50 mg (as Doxorubicin) freeze-dried vials
Batch No. TF/23874
Active Drug Substance Batch No. 0019

| Test | Initial control | 45° C. 1 mo. | 2 mos. | 3 mos. |
|---|---|---|---|---|
| Appearance | A | UNCHANGED | | |
| Assay (U.V. method) | | | | |
| mg/vial | 50.99 | 50.05 | 49.30 | 47.06 |
| % initial | 100.0 | 98.2 | 96.7 | 92.3 |
| Free doxorubicin content % (HPLC method) | 1.04 | 2.09 | 2.14 | 2.04 |
| Water % | 1.3 | n.d. | n.d. | n.d. |
| Reconstituted solution** | | | | |
| Reconstitution time (min) | 1.5 | 2.0 | 2.0 | 2.5 |
| Appearance | B | UNCHANGED | | |
| pH | 5.42 | 5.34 | 5.19 | 5.00 |

**25 ml of Water for Injections, BP
n.d. = not determined
A = colourless glass vials containing a porous, red freeze-dried cake or mass
B = clear and clean red solution, essentially free from visible particles of foreign matter

TABLE 5

Accelerated stability data of PK1 50 mg (as Doxorubicin) freeze-dried vials
Batch No. TF/23874
Active Drug Substance Batch No. 0019

| Test | Initial control | 55° C. 1 mo. | LCT + 100 F.C. 1 mo. |
|---|---|---|---|
| Appearance | A | UNCHANGED | UNCHANGED |
| Assay (U.V. method) | | | |
| mg/vial | 50.99 | 49.50 | 49.70 |
| % initial | 100.0 | 97.1 | 97.5 |
| Free doxorubicin content % (HPLC method) | 1.04 | 2.18 | 2.10 |
| Water % | 1.3 | n.d. | n.d. |
| Reconstituted solution** | | | |
| Reconstitution time (min) | 1.5 | 2.5 | 2.0 |
| Appearance | B | UNCHANGED | UNCHANGED |
| pH | 5.42 | 5.25 | 5.02 |

**25 ml of Water for Injections, BP
A = colourless glass vials containing a porous, red freeze-dried cake or mass
B = clear and clean red solution, essentially free from visible particles of foreign matter
LCT = Light Cabinet Temperature (28° ± 2° C.)
F.C. = Foot Candles
n.d. = not determined

TABLE 6

Long-term stability data of PK2 50 mg (as Doxorubicin) freeze-dried vials
Batch No. TF/23879
Active Drug Substance Batch No. 0057

| Test | Initial control | Refrigerator Temperature* | | | | | | |
|---|---|---|---|---|---|---|---|---|
| | | 1 mo | 2 mos | 3 mos | 6 mos | 9 mos | 12 mos | 18 mos |
| Appearance | A | UNCHANGED | | | | | | |
| Assay (U.V. method) | | | | | | | | |
| mg/vial | 49.38 | 50.05 | 46.75 | 45.76 | 47.67 | | | |
| % initial | 100.0 | 101.3 | 94.7 | 92.7 | 96.5 | | | |
| Free doxorubicin content % (HPLC method) | 0.09 | 0.26 | 0.25 | 0.25 | 0.22 | | | |
| Water % | 0.7 | n.d. | n.d. | n.d. | n.d. | | | |
| Reconstituted solution** | | | | | | | | |
| Reconstitution time (min) | 1.5 | 1.5 | 1.5 | 1.5 | 1.2 | | | |
| Appearance | B | UNCHANGED | | | | | | |
| pH | 5.42 | 5.42 | 5.39 | 5.24 | 5.07 | | | |

*2°–8° C.
**25 ml of Water for Injections, BP
n.d. = not determined
A = colourless glass vials containing a porous, red freeze-dried cake or mass
B = clear and clean red solution, essentially free from visible particles of foreign matter

TABLE 7

Long-term stability data of PK2 50 mg (as Doxorubicin) freeze-dried vials
Batch No. TF/23879
Active Drug Substance Batch No. 0057

| Test | Initial control | 25° C. | | | | | |
|---|---|---|---|---|---|---|---|
| | | 2 mos. | 3 mos. | 6 mos. | 9 mos. | 12 mos. | 18 mos. |
| Appearance | A | UNCHANGED | | | | | |
| Assay (U.V. method) | | | | | | | |
| mg/vial | 49.38 | 46.30 | 45.98 | 48.68 | | | |
| % initial | 100.0 | 93.8 | 93.1 | 98.6 | | | |
| Free doxorubicin content % (HPLC method) | 0.09 | 0.28 | 0.24 | 0.22 | | | |
| Water % | 0.7 | n.d. | n.d. | n.d. | | | |
| Reconstituted solution** | | | | | | | |
| Reconstitution time (min) | 1.5 | 1.5 | 1.5 | 1.2 | | | |
| Appearance | B | UNCHANGED | | | | | |
| pH | 5.42 | 5.29 | 5.17 | 5.00 | | | |

**25 ml of Water for Injections, BP
n.d. = not determined
A = colourless glass vials containing a porous, red freeze-dried cake or mass
B = clear and clean red solution, essentially free from visible particles of foreign matter

TABLE 8

Accelerated stability data of PK2 50 mg (as Doxorubicin) freeze-dried vials
Batch No. TF/23879
Active Drug Substance Batch No. 0057

| Test | Initial control | 35° C. | | | | |
|---|---|---|---|---|---|---|
| | | 1 mo. | 3 mos. | 6 mos. | 9 mos. | 12 mos. |
| Appearance | A | UNCHANGED | | | | |
| Assay (U.V. method) | | | | | | |
| mg/vial | 49.38 | 49.35 | 45.76 | 48.75 | | |
| % initial | 100.0 | 99.9 | 92.7 | 98.7 | | |
| Free doxorubicin content % (HPLC method) | 0.09 | 0.26 | 0.24 | 0.23 | | |
| Water % | 0.7 | n.d. | n.d. | n.d. | | |
| Reconstituted solution** | | | | | | |
| Reconstitution time (min) | 1.5 | 1.5 | 2.0 | 1.2 | | |
| Appearance | B | UNCHANGED | | | | |
| pH | 5.42 | 5.35 | 5.09 | 4.90 | | |

**25 ml of Water for Injections, BP
n.d. = not determined
A = colourless glass vials containing a porous, red freeze-dried cake or mass
B = clear and clean red solution, essentially free from visible particles of foreign matter

TABLE 9

Accelerated stability data of PK2 50 mg (as Doxorubicin) freeze-dried vials
Batch No. TF/23879
Active Drug Substance Batch No. 0057

| Test | Initial control | 45° C. | | |
|---|---|---|---|---|
| | | 1 mo. | 2 mos. | 3 mos. |
| Appearance | A | UNCHANGED | | |
| Assay (U.V. method) | | | | |
| mg/vial | 49.38 | 48.60 | 46.70 | 45.61 |
| % initial | 100.0 | 98.4 | 94.6 | 92.4 |
| Free doxorubicin content % (HPLC method) | 0.09 | 0.28 | 0.26 | 0.24 |
| Water % | 0.7 | n.d. | n.d. | n.d. |
| Reconstituted solution** | | | | |
| Reconstitution time (min) | 1.5 | 1.5 | 2.5 | 2.5 |
| Appearance | B | UNCHANGED | | |
| pH | 35.42 | 5.14 | 5.09 | 5.08 |

**25 ml of Water for Injections, BP
n.d. = not determined
A = colourless glass vials containing a porous, red freeze-dried cake or mass
B = clear and clean red solution, essentially free from visible particles of foreign matter

TABLE 10

Accelerated stability data of PK2 50 mg (as Doxorubicin) freeze-dried vials
Batch No. TF/23879
Active Drug Substance Batch No. 0057

| Test | Initial control | 55° C. 1 mo. | LCT + 100 F.C. 1 mo. |
|---|---|---|---|
| Appearance | A | UNCHANGED | UNCHANGED |
| Assay (U.V. method) | | | |
| mg/vial | 49.38 | 52.40 | 49.45 |
| % initial | 100.0 | 106.1 | 100.1 |
| Free doxorubicin content % (HPLC method) | 0.09 | 0.26 | 0.27 |
| Water % | 0.7 | n.d. | n.d. |
| Reconstituted solution** | | | |
| Reconstitution time (min) | 1.5 | 1.5 | 1.5 |

TABLE 10-continued

Accelerated stability data of PK2 50 mg (as Doxorubicin)
freeze-dried vials
Batch No. TF/23879
Active Drug Substance Batch No. 0057

| Test | Initial control | 55° C. 1 mo. | LCT + 100 F.C. 1 mo. |
|---|---|---|---|
| Appearance | B | UNCHANGED | UNCHANGED |
| pH | 5.42 | 4.98 | 5.51 |

**25 ml of Water for Injections, BP
A = colourless glass vials containing a porous, red freeze-dried cake or mass
B = clear and clean red solution, essentially free from visible particles of foreign matter
LCT = Light Cabinet Temperature (28° ± 2° C.)
F.C. = Foot Candles
n.d. = not determined

What is claimed is:

1. A lyophilized composition comprising (a) a conjugate comprising a N-alkyl methacrylamide-based copolymer linked through a peptide spacer to an anthracycline glycoside and (b) a cosolubilizing agent, wherein per 10 Parts by weight of said conjugate, there are from about 0.01 to 1.0 parts by weight of said cosolubilizing agent.

2. The lyophilized composition according to claim 1 wherein said N-alkyl methacrylamide-based copolymer is a copolymer of N-(2-hydroxypropyl) methacrylamide.

3. The lyophilized composition according to claim 1 wherein the anthracycline glycoside is daunorubicin, doxorubicin, epirubicin or idarubicin.

4. The lyophilized composition according to claim 1 wherein the peptide spacer is Gly-Phe-Leu-Gly.

5. The lyophilized composition according to claim 1 wherein the cosobulizing agent is a polysorbate, a polaxamer, a polyethylene glycol ester of a fatty acid or a phosphatide.

6. The lyophilized composition according to claim 5 wherein the cosolubilizing agent is selected from the group consisting of polysorbate 20, polysorbate 80, a poloxamer of formula $HO(CH_2CH_2O)_{75}.(CH(CH_3)CH_2O)_{30}.(CH_2H_2O)_{75}H$, a polyoxyethylene stearate and a lecithin.

7. The lyophilized composition according to claim 1, wherein said conjugate further comprises a targeting moiety linked through a peptide spacer to said N-alkyl methacrylate-based copolymer.

8. A lyophilized composition according to claim 7, wherein the targeting moiety is galactose, galactosamine, glucosamine, mannosamine, fucosylamine or lactosamine.

9. A lyophilized composition according to claim 1 wherein the conjugate is (i) a conjugate composed of x mol % of units of formula (A), y mol % of units of formula (B) and =mol % of units of formula (C):

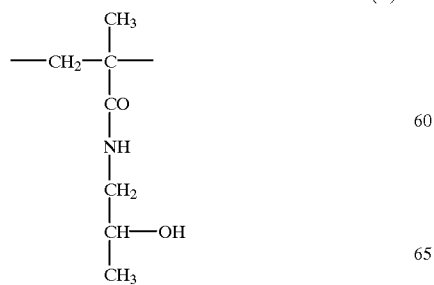
(A)

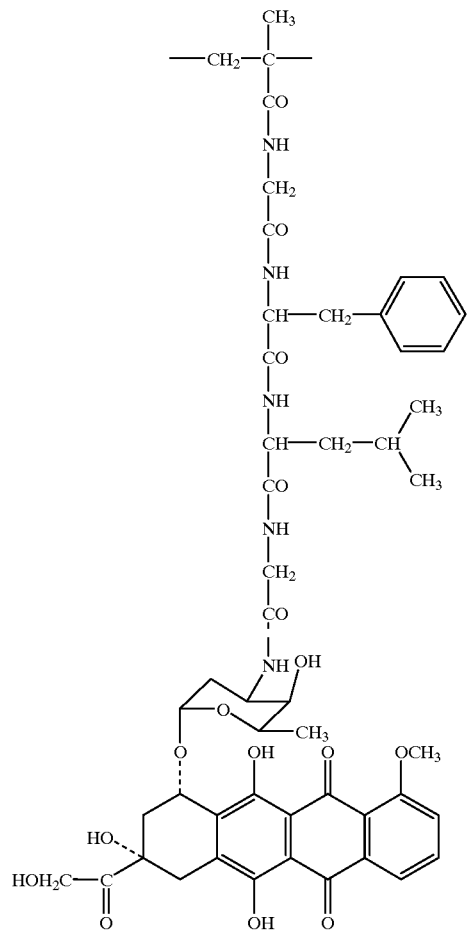
(B)

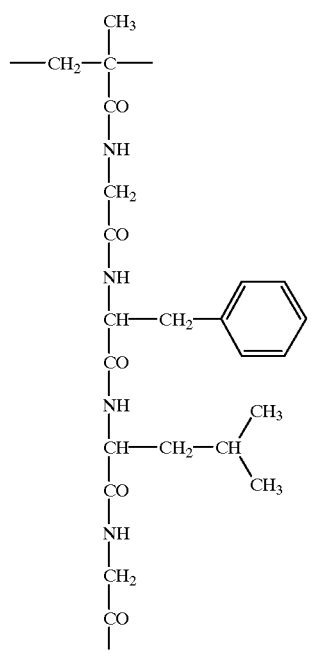
(C)

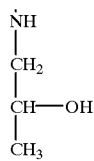

10. The lyophilized composition according to claim 1, which further comprises (c) a fillers wherein the weight ratio of said conjugate to said filler is about 0.1:1 to 20:1.

11. The lyophilized composition according to claim 10, wherein said filler is selected from the grout consisting of a sugar, a polyalcohol, an amino acid, a polyvinyl pyrrolidone, a polysaccharide or an inorganic salt.

12. The lyophilized composition according to claim 11 wherein the sugar is selected from the group consisting of glucose, maltose, sucrose or lactose.

13. A kit comprising:
(a) a lyophilized composition comprising (i) a conjugate comprising a N-alkyl methacrylamide-based copolymer linked through a peptide spacer to an anthracycline glycoside and (ii) a cosolubilizing agent, wherein per 10 parts by weight of said conjugate, there are from about 0.01 to 1.0 Parts by weight of said cosolubilizing agent; and
(b) a sterile solution for reconstituting said lyophilized composition.

14. A method for preparing a lyophilized composition which comprises (a) mixing, in aqueous solution, a conjugate comprising a N-alkyl methacrylamide-based copolymer linked through a peptide spacer to an anthracycline glycoside and a cosolubilizing agent, wherein per 10 parts by weight of said conjugate, there are from about 0.01 to 1.0 parts by weight of said cosolubilizing agent, and, optionally, a filler, wherein the weight ratio of said conjugate to said filler is about 0.1:1 to 20:1, and/or an organic solvent and (b) lyophilizing said aqueous solution.

15. A method for preparing an injectable aqueous solution, which method comprises reconstituting a lyophilized composition comprising (a) a conjugate comprising a N-alkyl methacrylamide copolymer linked through a peptide spacer to an anthracycline glycoside and (b) a cosolubilizing agent, wherein per 10 parts by weight of said conjugate, there are from about 0.01 to 1.0 Parts by weight of said cosolubilizing agent, with a sterile aqueous diluent.

16. The lyophilized composition according to claim 15 wherein said N-alkyl methacrylamide copolymer is a copolymer of N-(2-hydroxypropyl) methacrylamide.

17. The lyophilized composition according to claim 15 wherein the anthracycline glycoside is daunorubicin, doxorubicin, epirubicin or idarubicin.

18. The lyophilized composition according to claim 15 wherein the peptide spacer is Gly-Phe-Leu-Gly.

19. The lyophilized composition according to claim 15 wherein the cosobulizing agent is a polysorbate, a polaxamer, a polyethylene glycol ester of a fatty acid or a phosphatide.

20. The lyophilized composition according to claim 15, wherein said conjugate further comprises a targeting moiety linked through a peptide spacer to said inert polymeric carrier.

21. The lyophilized composition according to claim 1 wherein the alkyl groups of said N-alkyl methacrylamide based copolymer are $C_{1-6}$ alkyl groups.

22. The lyophilized composition according to claim 1 wherein the alkyl groups of said N-alkyl methacrylamide-based copolymer are substituted one or more times with hydroxy groups.

* * * * *